United States Patent [19]

Harris et al.

[11] Patent Number: 5,239,860
[45] Date of Patent: Aug. 31, 1993

[54] SENSOR FOR MEASURING ALCOHOL CONTENT OF ALCOHOL/GASOLINE FUEL MIXTURES

[75] Inventors: Stephen J. Harris, Birmingham; Stephen J. Swarin, Rochester; Michel F. Sultan, Troy; David K. Lambert, Sterling Heights, all of Mich.; Michael D. Jack, Goleta, Calif.

[73] Assignees: General Motors Corporation, Detroit, Mich.; Santa Barbara Research Center, Goleta, Calif.

[21] Appl. No.: 699,018

[22] Filed: May 13, 1991

[51] Int. Cl.⁵ .............................. G01N 21/35
[52] U.S. Cl. ...................... 73/61.48; 123/1 A; 250/339; 250/342
[58] Field of Search .......... 73/61.1 R, 61.48; 250/339, 341, 343

[56] References Cited

U.S. PATENT DOCUMENTS

| | | |
|---|---|---|
| 3,696,247 | 10/1972 | McIntosh et al. |
| 4,541,272 | 9/1985 | Bause ................. 73/118 |
| 4,594,968 | 6/1986 | Degobert et al. ........... 123/1 A |
| 4,770,129 | 9/1988 | Miyata et al. ............. 123/1 A |

FOREIGN PATENT DOCUMENTS

| | | |
|---|---|---|
| 304230 | 2/1989 | European Pat. Off. ........ 250/339 |
| 9003565 | 4/1990 | PCT Int'l Appl. |

*Primary Examiner*—Hezron E. Williams
*Assistant Examiner*—Joseph W. Roskos
*Attorney, Agent, or Firm*—George A. Grove; Domenica N. S. Hartman

[57] ABSTRACT

An alcohol sensing device is provided for determination of the alcohol content within an alcohol/gasoline fuel mixture which is being provided for the operation of an internal combustion engine. The sensing device uses infrared spectrometry measuring techniques. The infrared sensing device determines the ratio of light absorption by the alcohol/gasoline mixture at two discrete wavelengths within the near-infrared spectrum. The two particular wavelengths of interest are preferably chosen so that at one of the infrared wavelengths, alcohol is strongly absorbing while the gasoline exhibits very little absorption, and at the second wavelength both the alcohol and the gasoline exhibit are essentially non-absorbing. An alternating current is used to switch the light beam between two power settings so as to vary the intensity of transmitted light at both wavelengths. The light beam is transmitted through the alcohol/gasoline fuel mixture so that the two discrete wavelengths traverse the same optical path. Two detectors are adjacently disposed so as to receive the emitted light from each wavelength after their transmission through the alcohol/gasoline fuel mixture. Once the signals corresponding to the two wavelengths are obtained, the ratio of the absorbances by the fuel mixture at both wavelengths is computed. From this ratio, and the temperature of the fuel mixture, the concentration of alcohol in the fuel is determined.

18 Claims, 2 Drawing Sheets

SENSOR FOR MEASURING ALCOHOL CONTENT OF ALCOHOL/GASOLINE FUEL MIXTURES

This invention generally relates to a sensor for detecting the alcohol concentration within an alcohol-containing gasoline fuel mixture which is provided to an automotive internal combustion engine. More particularly, this invention relates to an alcohol sensor which determines the alcohol concentration within such a fuel mixture using infrared spectroscopy, wherein a light beam emitting at near-infrared wavelengths is transmitted through the fuel mixture and the ratio of infrared absorbances by the mixture at two discrete wavelengths is determined.

BACKGROUND OF THE INVENTION

Automobiles which can operate on alternative fuels, such as arbitrary mixtures of alcohol and gasoline, are indicative of future trends and, in fact, will soon be required by law in certain regions. For proper engine operation it will be necessary to measure the ratio of alcohol-to-gasoline within the fuel mixture which is being injected into the combustion chamber. Since the automobile may be filled with gasoline at one instance and an alcohol-containing gasoline mixture of up to about 85% methanol at the next, and because alcohol and gasoline can physically separate in the gas tank, this ratio may change very rapidly over a few minutes or even faster. Therefore, it is necessary that this ratio be determined continuously.

A variety of techniques have been previously proposed for making these on-board measurements of the alcohol content within the fuel mixture for control of the engine parameters. Typically, these methods have measured various properties of the gasoline mixture, including the dielectric constant, thermal conductivity, index of refraction, change in the speed of sound through the mixture and microwave absorption. However, these methods tend to be prohibitively expensive for widespread use or the measuring techniques involved are inherently problematic since they tend to be strongly dependent on temperature and/or the detailed properties of the gasoline used. Further, as an exacerbation of these shortcomings, the composition of a particular gasoline mixture may vary considerably even within a single name brand. Therefore, these methods have failed to provide the reliability required for automotive engine control applications.

An alcohol sensing device based on infrared spectroscopy methods would generally avoid the problems associated with these previous methods, including the strong dependence on temperature and/or the gasoline composition. This is because infrared spectroscopy is an analytical technique which measures the relative absorption of various infrared wavelengths by a particular specimen and is thereby dependent on the molecular constitution of the specimen. A sensor for determining the alcohol content in gasoline which utilizes such an infrared absorption technique is disclosed in U.S. Pat. No. 4,594,968 to Degobert et al, entitled "Process and Device for Determining the Composition of an Alcohol-Petrol Mixture, Adapted to the Automatic Regulation of Engines Fed with Fuel Mixtures Having a Variable Alcohol Content" issued, Jun. 17, 1986. However, there are many drawbacks associated with the use of this alcohol sensor, even though it utilizes the preferred infrared spectroscopy measurement techniques.

Degobert et al measure the alcohol content of the fuel mixture by determining the infrared absorbance of the fuel in the wavelength range between 0.7 and 1.7 micrometers. However, a reference measurement must first be made so that the intensity of the transmitted light through the fuel mixture can be referenced to the intensity of the original light source, for determination of the amount of absorbance. Degobert et al propose that the light beam be split, with one beam passing through an alcohol or gasoline/alcohol reference cell with known composition and the other beam passing through the fuel to be measured. This setup leads to several practical problems.

The Degobert et al system utilizes a beamsplitter, two sets of windows and two different detectors corresponding to both the reference and measuring cells. If any of these components change with time, which is extremely likely to occur particularly in the automobile environment, the signal from the device will be in error. For example if the inside of the measuring detector window becomes covered with a film from the fuel but the reference detector window stays relatively clean, then the measuring detector will sense relatively less light and the sensor will calculate a higher than correct alcohol content. The device fails to deal satisfactorily with the possibility that one window may become dirtier than the other.

In addition, the beamsplitter may become dirty in a way which will affect one light path more than the other, which again is a definite possibility in the dirty environment of an automobile. Also, it is extremely difficult to maintain the integrity of optical components which are exposed to flowing gasoline, as is the situation with the device of Degobert et al. For these reasons it is clear that it would be desirable to provide a sensing device which does not utilize a beamsplitter which duplicates optical paths and components for both the measuring and reference fuel sample cells, and which thereby avoids the shortcomings of the prior art.

Further, although this type of device proposed by Degobert et al utilizes infrared absorption spectroscopy, it is still strongly dependent on temperature due to the nature of its detection system. Within the engine environment of an automobile, the temperatures may fluctuate greatly over a wide range from about $-40°$ C. up to about $120°$ C., making it difficult in practice to maintain the two relatively large detectors and sample cells of this device at identical temperatures unless they are independently thermostated. If the detectors are at different temperatures, the absorbance measurements will give erroneous results. The output voltage of the LED source is also temperature sensitive and would therefore have to be thermostated to ensure reliable results. Lastly, the infrared absorption coefficient for alcohol is temperature dependent, thereby requiring two separate temperature measuring devices (one for the fuel measurement and one for the reference measurement). These various thermal outputs must all be incorporated into the algorithm used for determining the air-fuel ratio in order to ensure an accurate measurement.

It is clear that these requirements all add substantially to the complexity and cost of the device. Therefore, it would be desirable to provide an alcohol sensor for determining the alcohol content in a fuel mixture for use in an automobile environment, which utilizes infrared absorption spectroscopy techniques but which alleviates the many shortcomings associated with the previously proposed devices. In particular, it would be desirable to provide such an alcohol sensor which does not require the use of a beamsplitter for duplicate sample cells, and which is not strongly dependent on temperature effects or the particular fuel mixture composition.

SUMMARY OF THE INVENTION

It is an object of the present invention to provide an alcohol sensing device for use in determining the alcohol content within an alcohol-containing gasoline mixture.

It is a further object of this invention that such an alcohol sensing device utilize infrared spectroscopy techniques for determination of the relative absorption by the alcohol/gasoline fuel mixture at two discrete near-infrared wavelengths.

It is still a further object of this invention that the alcohol sensing device transmit a single light beam through the alcohol/gasoline fuel mixture for incidence upon a single substrate having two adjacently disposed detectors which are each filtered to receive a corresponding one of the two near-infrared wavelengths.

In accordance with a preferred embodiment of this invention, these and other objects and advantages are accomplished as follows.

A sensing device is provided for determination of the alcohol content within an alcohol-containing gasoline mixture, wherein this fuel mixture is provided via a fuel carrying line to an internal combustion engine for operation of that engine. The alcohol sensing device of this invention utilizes infrared spectroscopy measuring techniques and is capable of detecting alcohols without any interference from the presence or absence of gasoline.

The alcohol sensing device contains a single light source which emits a spectrum of light including the near-infrared wavelengths. The sensor measures the ratio of light transmission (or conversely—light absorption by the fuel mixture) at two discrete wavelengths within the near-infrared spectrum. Alcohols will generally absorb different wavelengths of light as compared to alcohol-free gasolines because the alcohols contain oxygen-hydrogen (O—H) bonds while gasolines practically do not. Therefore, the two particular wavelengths of interest are preferably chosen so that at one of the infrared wavelengths, alcohol is strongly absorbing because of the vibrational overtone transition associated with the O—H bond in the alcohol molecule. At this same wavelength however, the gasoline is more transparent, i.e., exhibits very little absorption, since the gasoline does not contain practically any O—H bonds. The second wavelength is chosen so that both the alcohol and the gasoline exhibit little absorption of the infrared wavelength and are therefore nearly transparent.

As an illustrative example, the fundamental vibrational transition wavelengths in alcohols are in the range of 2.8-2.9 micrometers while the shortest wavelength in alcohol-free gasoline is about 3.2 micrometers. Vibrational overtone transitions, which are infrared absorbing, are at roughly half of these wavelengths, one-third of these wavelengths and so on. Therefore, the detection of the alcohol within the fuel mixture can be made at predetermined wavelengths without any interference or absorption by the gasoline, just by appropriately choosing those wavelengths of interest. Specifically, the alcohol sensor of this invention compares infrared light transmission between two preferred spectral bands, one centered at about 1.5 micrometers wavelength where absorption by only the alcohol occurs and the other at about 1.3 micrometers wavelength where virtually no absorption occurs.

During operation of the sensor, which will correspond with the operation of the internal combustion engine receiving the alcohol-containing gasoline mixture, the light source alternates between a high power and low power setting. At both settings, a beam of light is emitted which contains the two discrete wavelengths within the near infrared spectrum. The light beam is transmitted through the alcohol/gasoline fuel mixture which is being carried within the fuel line to the internal combustion engine, such that the two discrete wavelengths traverse the same optical path. Two detectors are adjacently disposed so as to receive the emitted light from each wavelength after their transmission through the alcohol/gasoline fuel mixture.

The first detector determines the amount of infrared absorbance by the fuel mixture at the first wavelength by filtering all other wavelengths except the first wavelength of interest. Similarly, the second detector determines the amount of infrared absorbance by the fuel mixture at the second wavelength. The two detectors are thermopile detectors which convert the received light into heat. Accordingly each of the two thermopile detectors generates an increase in temperature corresponding to the amount of transmitted light received at the two particular wavelengths. The temperature increases are then measured. Once these signals for the two wavelengths are obtained, the ratio of the amounts of absorption by the alcohol/gasoline fuel mixture at both wavelengths is computed. The concentration of alcohol in the fuel is then determined from standard absorption data.

A few of the particularly advantageous features associated with the sensor of this invention are that a single optical path is used for both wavelengths of interest, and that the critical parameter being measured is the ratio of the relative absorbances at two different wavelengths at both power settings for the light source. Therefore, any degradation of the light source or the detector windows will equally affect the measurements for both wavelengths and will essentially cancel out in the final ratio determination. In addition, both of the thermopile detectors are extremely small and are mounted on a much larger carrying substrate which serves, in part, as a heat sink. Therefore practically speaking, any external temperature effects experienced by the detectors will be identical for both of the detectors and again, these potentially detrimental effects will accordingly cancel since it is the ratio between the two measurements which is critical. Also, since a light bulb is utilized as the light source, the spectral output of the bulb is essentially independent of local temperature. Lastly, the number of components (and correspondingly the complexity) within the sensor is minimized, which thereby tends toward an affordable sensor for automotive applications.

Other objects and advantages of this invention will be better appreciated from the detailed description thereof, which follows.

BRIEF DESCRIPTION OF THE DRAWINGS

The above and other advantages of this invention will become more apparent from the following description taken in conjunction with the accompanying drawing wherein.

DETAILED DESCRIPTION OF THE PREFERRED EMBODIMENTS

In accordance with this invention, an alcohol sensing device is provided for determination of the alcohol content within an alcohol/gasoline fuel mixture which is being provided for the operation of an internal combustion engine. The sensing device uses infrared spectrometry measuring techniques and is capable of detecting the amount of alcohol without any interference from the presence of gasoline. The infrared sensing device determines the ratio of light transmission through the alcohol/gasoline mixture at two discrete wavelengths within the near-infrared spectrum.

Within the near-infrared wavelength range of about 1.2 to 2.4 micrometers (slightly longer wavelengths than visible light), absorption spectra for alcohol and gasoline are substantially different, making the near-infrared spectra particularly suited for these types of measurements. The alcohol, which may constitute up to 85% by volume of an alcohol/gasoline fuel mixture, is primarily in the form of either ethanol or methanol, while gasoline is a mixture of volatile hydrocarbons with the major components being branched-chain paraffins, cycloparafins and aromatics. Alcohol will absorb light at wavelengths which are different than alcohol-free gasoline because the alcohols contain oxygen-hydrogen bonds while gasoline generally does not.

Preferably, the two particular wavelengths are chosen so that at the first wavelength the alcohol is strongly infrared-absorbing because of a vibrational overtone transition of the O—H bond within the alcohol molecule. At this same wavelength the gasoline which is characterized by a virtual absence of O—H bonds does not absorb and is correspondingly more transparent. At the second wavelength both alcohol and gasoline exhibit negligible absorption of the infrared wavelength and are therefore nearly transparent.

More specifically, the fundamental transition wavelengths in alcohols are in the range of 2.8–2.9 micrometers while the shortest wavelength in alcohol-free gasoline is about 3.2 micrometers. Overtone transitions which cause absorbance by the molecule occur at roughly half these wavelengths within the near-infrared spectrum, or about 1.4 and 1.6 micrometers respectively for the alcohol and the gasoline. Absorbing overtone transitions also occur at about one-third of these wavelengths, and could be determined if necessary by other means. Therefore, the detection of the alcohol can be made by measuring the absorbance at the particular wavelength without any interference or absorption by the gasoline.

Figure 1:
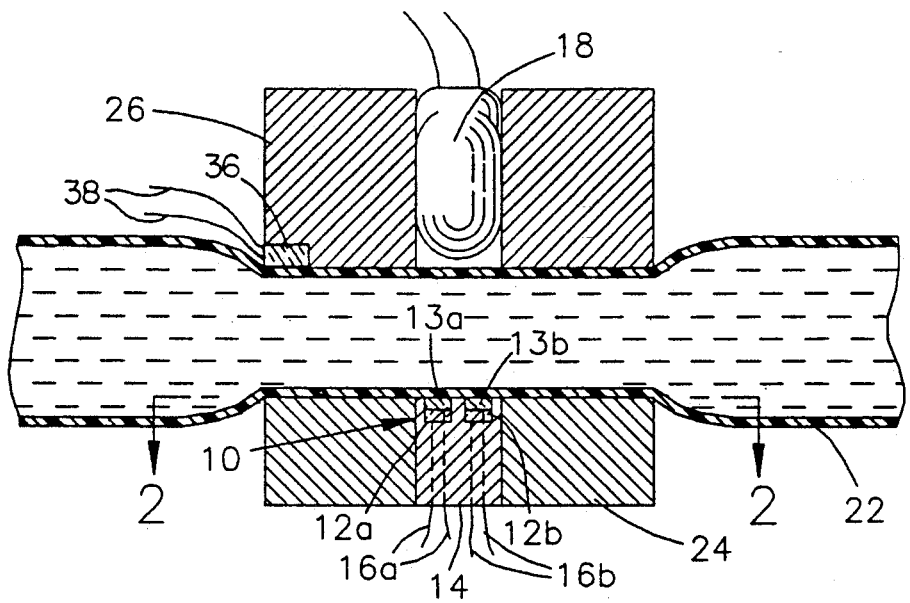
FIG. 1 is a cross-sectional view of the alcohol sensor in accordance with this invention for detection of the alcohol concentration within an alcohol/gasoline fuel mixture which is provided to an internal combustion engine via a fuel carrying line.

The alcohol sensing device of this invention is shown cross-sectionally in FIG. 1. The sensor basically consists of a single light source 18, a dual element thermopile detector 10, and fixturing means 24 and 26 for retaining the light source 18 in a manner so that it transmits its emitted light through the fuel carrying line 22 to be incident upon the dual element detector 10.

As shown, the sensor detects the alcohol content of the fuel mixture which is being carried within a fuel carrying line 22, such as for the operation of an internal combustion engine within an automobile. At the desired region where the alcohol detection is to occur, the conventional fuel line, which is typically a ⅜" diameter metal tube, is converted to a ⅜" diameter tube 22 of a suitable material which is transparent and chemically resistant to attack by alcohols and gasoline. (The diameter of the converted tubing is to be identical or compatible with the diameter of the conventional metal tubing used elsewhere in the fuel line, and is therefore dependent on the size of the fuel line tubing used.) The conversion between the metal fuel line and the transparent tubing 22, in the region where detection is to occur, is accomplished using conventional fittings (not shown).

A preferred material for the fuel carrying line 22 would be fluorinated ethylene polymers, such as the commercially available material Teflon, some forms of which are transparent at the wavelengths of interest and are chemically resistant to alcohols and gasoline. It is noted though that only the clear Teflon tubing was found to be suitable for the fuel line 22. The clear Teflon tubing 22 transmitted a much larger fraction of the infrared light than did white Teflon. For these reasons, the clear Teflon is most preferred. It is foreseeable that other suitable materials which are transparent to the desired wavelengths and also chemically resistant to the fuel mixture could be substituted.

In order to obtain the desired optical path length for transmission of the infrared wavelengths through the fuel mixture, the tubing 22 is compressed appropriately to form the desired path length in that region where detection will occur. It is to be noted that the preferred tubing 22 material is relatively easy to compress. As shown more clearly in FIG. 3, the tubing 22 is compressed as it passes through a gap 30 between two metal plates 24 and 26 which are attached to each other by four screws 28. The screws 28 allow the width of the gap 30 to be adjusted depending on the desired optical path length. The plates 24 and 26 are formed from any metal which will withstand the environmental extremes within the automobile while not being practically prohibitive. For demonstrational purposes, the plates 24 and 26 were formed from aluminum, however it is not necessary that they be formed from such material. In addition, one of the plates 26 was larger at about 25×32×22 millimeters than the other 24 which was about 25×32×7 millimeters, since the larger plate 26 held the light source 18. Actually, plates 24 and 26 are not necessary so long as some form of rigid fixturing means is provided.

Figure 2:
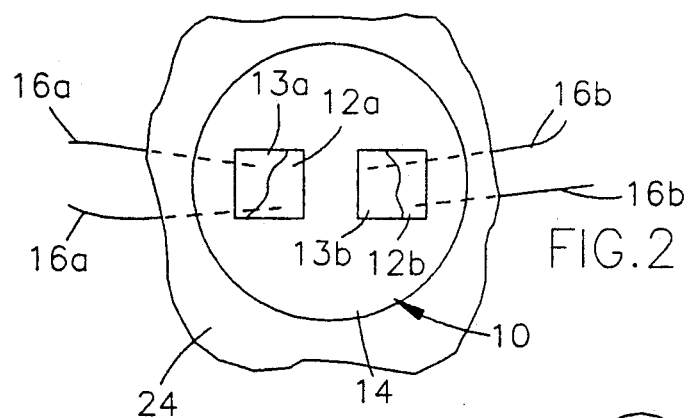
FIG. 2 is a plan view of the two thermopile detectors provided on the carrying substrate shown in FIG. 1 for detection of the incident light at two discrete wavelengths.

The appropriate optical path length for transmission of the near-infrared wavelengths through the fuel mixture within the fuel line 22, (represented by the width of the gap 30 between metal plates 24 and 26 as shown in FIG. 2) should not be so large that it results in all of the transmitted light being absorbed by the fuel mixture within the fuel line 22. Nor should the optical path length (30) be so small that absorption is negligible. This determination of the appropriate path length will be discussed more fully later, yet optimum results appear to be realized with an optical path length (30) ranging between one and three millimeters for the wavelengths of interest.

Again as illustrated in FIG. 1, the sensor consists of a single light source 18, mentioned previously as being held within the larger aluminum plate 26. The single light source 18 emits white light at the near-infrared wavelengths of interest. The light source 18 is preferably a quartz-envelope tungsten-halogen light bulb. Such a type of light bulb 18 is commercially available from Gilway Technical Lamp of Woburn, Mass., Part No. L1041. This particular lamp 18 runs at a peak current of generally between 1.2 and 1.4 amps, with the maximum operating parameters specified as 1.43 amps and 5 Volts. The light bulb 18 can be expected to have a life of approximately 5000 hours, thereby requiring few, if any, replacements during the life of the vehicle. This light bulb 18 is preferred because it has a lens on the front end to concentrate the incident light on the detector 10, resulting in a larger signal from the detector 10.

Held within the smaller metal plate 24, is a dual-element thermopile detector 10, shown in both FIGS. 1 and 2. As more closely seen in FIG. 3, the dual element detector 10 consists of two individual thermopile detectors 12a and 12b provided on an appropriate substrate 14. External electrical connection wires 16a and 16b extend from each detector 12a and 12b. Generally, a thermopile detector (12a or 12b) contains many thermocouples which are electrically connected in series so that their individual voltages are cumulative. The thermopile detector (12a or 12b) converts incident infrared light into heat, and produces a voltage proportional to the resulting increase in temperature. The preferred dual element thermopile detector 10 used in the specific embodiment of this invention was a DR34 dual element thermopile detector from Dexter Research Inc. of Dexter, Mich.

Figure 3:
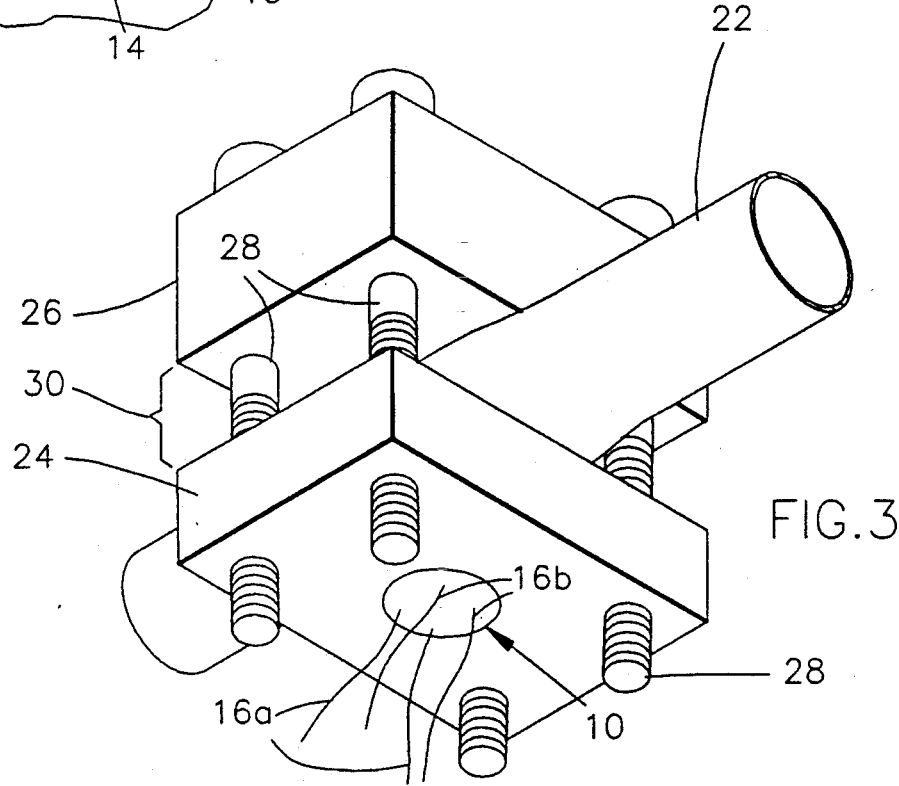
FIG. 3 is an elevated view of the alcohol sensor shown in FIG. 1.

As shown more closely in FIG. 3, the DR34 dual element detector (10) contains two miniaturized multi-junction thermopiles 12a and 12b. The two thermopiles 12a and 12b are made from interdigitated thin films of evaporated bismuth and antimony, which are covered with an energy absorbing smoke black film. The smoke black film absorbs spectral wavelengths from the ultraviolet to the far-infrared and is deposited onto the two interdigitated active junction areas (depicted as 12a and 12b) which are approximately 3.16 millimeters×0.4 millimeters×1.4 millimeters in volume, and which are separated from each other by a distance of about 0.5 millimeters. The two thermopile detection elements 12a and 12b are hermetically sealed under a purged atmosphere of Argon or Nitrogen and appropriately heat treated to ensure long term stability. The final package 10 is resistant to both mechanical and temperature shock.

The thermopiles 12a and 12b are capable of operating within the temperature range experienced within an automobile engine compartment of about $-40°$ C. and $120°$ C. and are also sufficiently sensitive and accurate over this temperature range in the acoustically noisy environment of the engine compartment. In addition, since the thermopiles 12a and 12b are voltage generating devices, they do not require application of a current or bias voltage for operation. They are also compatible with conventional electrical connections. Lastly and perhaps most significantly, the thermopiles 12a and 12b respond sufficiently close to linearly up to the maximum power that needs to be detected. Specifically, in the preferred embodiment the maximum optical power absorbed by the detector is approximately one milliWatt, giving a temperature rise of 3.1 degrees Centigrade. Detector response changes by about 0.004 per degree Centigrade, so at the maximum power level the detector is expected to deviate by a factor of about 0.012 from linear response. The effect of this non-linearity on sensor output is negligible. However, it is noted that over a large temperature range, such as over 100 degrees Centigrade, the sensor would become quite non-linear.

Figure 4:
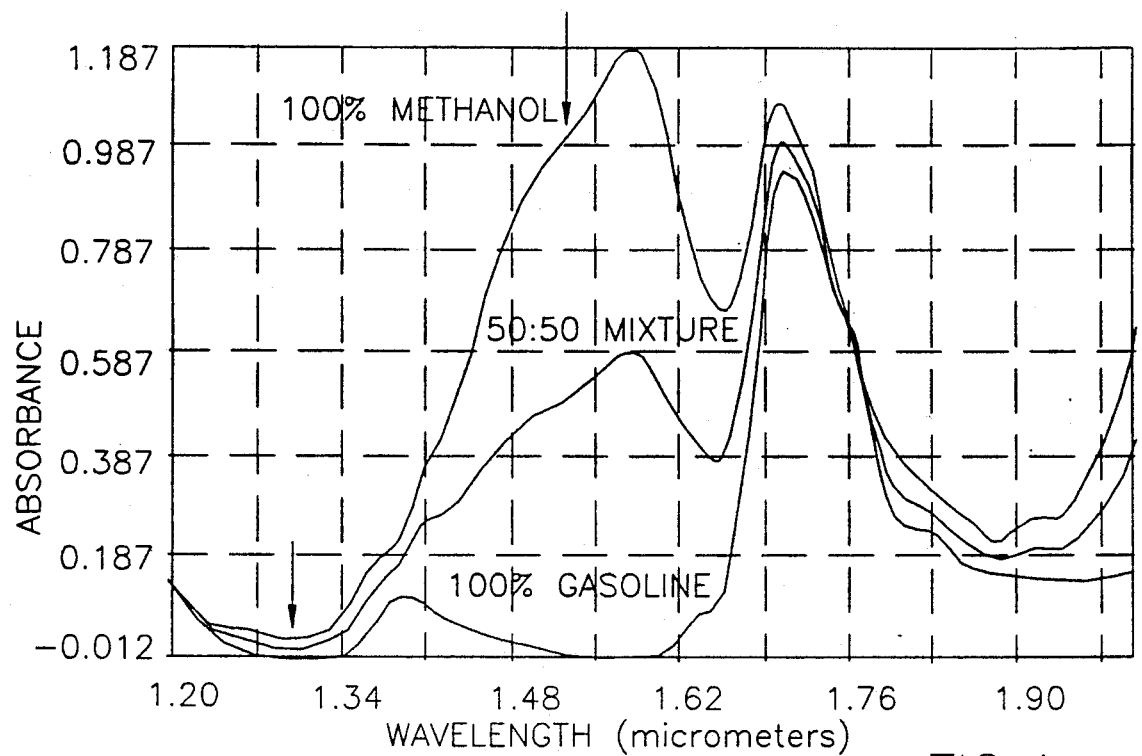
FIG. 4 is a graph showing relative absorbance versus near-infrared wavelength in micrometers, for 100% methanol, 100% gasoline and a 50:50 mixture of each.

As stated previously, the preferred thermopile detectors 12a and 12b absorb the preferred wavelengths of interest with this invention. The alcohol sensor of this invention compares infrared light transmission between two preferred spectral bands, one centered at about 1.5 micrometers wavelength and the other at about 1.3 micrometers wavelength. As shown in the graph of FIG. 4, which depicts the relative absorbance at near-infrared wavelengths (in micrometers) for methanol, gasoline and a 50:50 mixture of each, there is a vibrational overtone transition of alcohol associated with the O—H molecular bonds which is centered at about 1.5 micrometers, at which the alcohol absorbs the infrared light and the gasoline does not. At about 1.3 micrometers, neither the alcohol or gasoline absorb much of the infrared light. The parameters which were considered for choosing the particular wavelengths of interest are discussed more fully later, however, it is important to note that these preferred wavelengths of 1.3 and 1.5 micrometers are within the range of absorbing wavelengths for the thermopiles 12a and 12b.

With this arrangement, it should be noted that it is also foreseeable that light could be detected at more than two wavelengths in order to gain more information about the fuel mixture, such as the temperature, octane number, boiling point or other parameters. This would best be accomplished by providing a third (or more depending upon the amount of information desired) thermopile element on the detector 10 which is filtered to receive the third wavelength of interest.

In addition, although the thermopile detectors 12a and 12b are most preferred, there are other types of infrared detectors that operate at 1.5 micrometers wavelength or less which could be suitable for this application. However, these alternative detectors are typically limited by their range of operational temperatures, sensitivity to vibration and noise, and/or cost, and therefore would not lend themselves to the widespread use envisioned by this invention. The thermopile detectors 12a and 12b appear to optimize these concerns and are therefore preferred.

Some of these alternative, but lesser preferred, detectors include the inexpensive type of PbS semiconductive devices. However, they are not designed to operate at the relatively high temperatures experienced within an engine compartment. In addition, semiconductor materials having an appropriate band gap and which use either a photoconductive or photovoltaic effect for sensing incident infrared light, such as $In_xGa_{1-x}As$ or $Hg_xCd_{1-x}Te$ materials, are more sensitive than thermopiles to infrared light at the lower end of the temperature range. However, as the temperature of the semiconductor material increases, sensitivity is reduced due to the thermally activated current within the semiconductor.

Another type of possible infrared detector which is similar to the thermopile detector (12a or 12b), in that it also converts infrared light into heat and then measures the resulting temperature increase, is the pyroelectric type of detector. Although pyroelectric detectors can be made to be as sensitive to incident light as thermopile detectors, they are not as suitable for use in acoustically and vibrationally noisy environments like the engine compartment of an automobile, since all pyroelectric materials are also piezoelectric which thereby results in a microphone effect when vibrated. For these various reasons, it is preferred to use the thermopile detectors (12a and 12b), such as those previously described, as the infrared detectors.

To successfully use a dual element thermopile detector 10 for measuring the alcohol content within a fuel mixture, first the optical throughput to each thermopile 12a and 12b must be maximized. This is accomplished by choosing an appropriate (1) pair of optical filters 13a and 13b to filter the desired wavelengths of interest, (2) optical path length (represented as gap 30) for transmission of the infrared light through the fuel within the fuel line 22, (3) material for the transparent fuel line 22, (4) optical infrared light source 18 and (5) relative position of the light source 18 and thermopile detectors 12a and 12b.

The next consideration is the electronic measuring circuitry. The preferred electronic measuring system performs as follows. The incandescent light bulb 18 is periodically switched between two values, a relatively high power and a relatively low power to alleviate any drifts in the resulting signal due to ambient temperature changes. Concurrently, the corresponding dc voltages which are generated by the temperature increase of the two thermopiles 12a and 12b are recorded. The recorded voltages for each switching cycle are used to compute a ratio, which is proportional to the ratio of the intensities of the transmitted light from the light source 18 at both chosen wavelengths of interest. This ratio can then be used to determine the alcohol content at a given temperature. For an extremely accurate sensor, a temperature measurement or compensation is required and preferred, since the infrared absorption of alcohol in the 1.5 micrometer band is slightly temperature dependent. It is therefore desirable to measure the temperature of the fuel mixture with a separate thermistor or thermocouple.

The desired wavelengths of interest, which determined the particular optical filters 13a and 13b used, were chosen as follows. In order to obtain the required absorption measurements for each of the two discrete wavelengths, optical filters which permit transmission of only those desired wavelengths at each thermopile 12a and 12b were necessary and installed onto the detecting areas of each thermopile 12a and 12b. In choosing the optical filter, the objective was to choose a filter which would result in the maximum degree of sensitivity for a corresponding change in the alcohol concentration within the fuel mixture.

According to our theoretical model, sensitivity to a change in the alcohol concentration was optimized by choosing a 1.5 micrometer filter that passed a band of wavelengths that was approximately the same as the alcohol spectral band in this wavelength region. This is a center wavelength of about 1.53 micrometers and transmission of light from about 1.43 to about 1.63 micrometers. As stated previously and as shown in FIG. 4, in this region identified by the right-most identifying arrow, the alcohol (methanol) is strongly infrared absorbing while the gasoline is not. A commercially available interference filter with approximately these optimum characteristics is Oriel Corporation's model 58045 with a center wavelength of 1.5 micrometers and 0.09 micrometer half band-width. A similar interference filter with a center wavelength of about 1.3 micrometers, Oriel model 58043, was used for the reference measurement wherein both the alcohol and the gasoline are non-absorbing, or relatively transparent, as identified in FIG. 4 by the left-most identifying arrow. The filters are interference filters, which reflect all wavelengths except the particular spectral band being filtered. The use of these two filters is preferred since they have comparable spectral transmission which helps limit problems of cross-talk between the two thermopile detectors 12a and 12b.

Although the preferred wavelengths for measurement of absorbance are approximately 1.3 and 1.5 micrometers because at the first wavelength there is relatively no absorption by either component and strong absorption by only the alcohol at the second wavelength, it is clear from FIG. 4 that the wavelengths of interest could range between about 1.25 to 1.35 micrometers and between about 1.4 to 1.6, respectively.

Specifically the purchased optical filters were each circular, approximately 25.4 millimeters in diameter, and cut using a diamond saw to a rectangular piece of about 2×4 millimeters. Each of the rectangular filters 13a and 13b were permanently attached to a corresponding thermopile 12a or 12b, so that each filter covered the sensitive area on its corresponding thermopile detector 12a or 12b.

Our theoretical model was also utilized to determine the preferred optical path length (represented by gap 30) through the alcohol/gasoline fuel mixture. Generally, the model showed that for low concentrations of alcohol within the fuel mixture, i.e., less than 50% by volume alcohol, a long path length produces a high degree of sensitivity corresponding to a change in the alcohol concentration. However, at high concentrations of alcohol, i.e., greater than about 50% by volume alcohol, the sensitivity is diminished by a long path length. This is because much of the incoming infrared light is absorbed by the alcohol over the long path length.

Therefore, it was determined that the optimum path length (30) maximizes the change in light intensity per the change in the alcohol concentration at the maximum alcohol concentration, which is approximately 85% alcohol in the alcohol/gasoline mixtures. In practice, this optimum occurs when the incident light intensity for a maximum alcohol concentration of about 85% by volume is about 50% of the incident light intensity when the alcohol concentration is equal to zero.

Specifically, according to both this spread sheet model and experimental data, it was determined that with the 1.5 micrometer wavelength filter, (which is where alcohol is absorbing and gasoline is not) an optical path length of about one to three millimeters for transmission of the infrared light through the fuel mixture is optimum. In the actual embodiment, a path length (30) of approximately two millimeters was utilized. The optical path length (30) of two millimeters resulted in an incident light intensity, at an alcohol concentration of about 85% by volume, which was about half the intensity at an alcohol concentration of zero. It was further determined that, in general, the optimum optical path length (30) is inversely proportional to the maximum alcohol concentration which is to be measured. To form this preferred optical path length (30), of about two millimeters in the specific example, the fuel line 22 was compressed accordingly between the two metal plates 24 and 26, as shown in FIGS. 1 and 2.

In practice, it is noted that parameters which were not considered by the model affect the choice of filters 13a and 13b and path length 30. Stray light reaching each of the thermopile detectors 12a and 12b is one such consideration, such as from environmental light or when the emitted light is carried around the fuel line 22 by multiple reflections, thereby not passing through the fuel at all. The optical filters 13a and 13b also pass some of the emitted light which is outside of the desired band of frequencies. However, these problems are diminished as the amount of emitted light in the desired wavelength range is increased. Avoidance of these stray light effects is another reason for using the previously described preferred optical filter 13a and 13b, which has a relatively large band width of about 0.2 micrometers and which therefore covers much of the alcohol absorption band.

Once signals at two (or more) wavelengths are obtained the concentration of the alcohol within the alcohol/gasoline fuel mixture is determined as follows. The temperature of the fuel mixture is measured and the signals are appropriately ratioed to determine the transmitted intensity at each wavelength. The ratio is equal to the difference in voltage outputs corresponding to the change in light intensity (between the high and low power settings of the light source) at the first detector sensing transmission at the first wavelength, divided by the difference in voltage outputs corresponding to the change in light intensity (between the high and low power settings) at the second detector sensing transmission at the second wavelength. an illustrative equation is as follows:

$$R = (V_{1A} - V_{1B})/(V_{2A} - V_{2B}),$$

where R is the ratio of absorbances, $V_{1A}$ and $V_{1B}$ are the voltage outputs by the first detector sensing at the first wavelength corresponding to the high and low power settings respectively, and $V_{2A}$ and $V_{2B}$ are the voltage outputs by the second detector sensing at the second wavelength corresponding to the high and low power settings respectively. The ratio is then compared to standard calibration curves for absorbance at that temperature.

Note that in order to determine the relative intensities it is not necessary that the two wavelengths, are chosen such that only one of the components, i.e., the alcohol, absorbs at a particular wavelength, such as in the preferred embodiment. It is only necessary that the absorbances of gasoline and of the alcohol differ from each other at least one of the two wavelengths. However, this latter mode of operation is less preferred, since with the preferred mode of measurement the relative measurements at the two wavelengths are more distinct because there is a clear absorption at one of the wavelengths which is attributable only to the one component.

In order to maximize the detected signal by the thermopiles 12a and 12b, it was desirable to position the detector 10 close to the fuel line 22. The distance between the detector 10 and the clear tubing 22 may be adjusted by modifying the position of the detector 10 within the fixturing plate 24. By placing the detector 10 flush against the tubing 22, the resulting signal from the detector 10 is increased due to the higher intensity of incident light. By moving the detector 10 further away from the tubing 22, the resulting electrical signal is diminished but the effects of small nonuniformities in the light transmission through the tubing 22 (such as caused by a fleck of dirt on the fuel line) are reduced. In the experimental set-up, the detector 10 was pressed flush against the fuel line tubing 22 so as to achieve the maximized signal. However, in an automotive environment these concerns must be optimized and may require different placement of the detector 10 within its retaining plate 24 or use of a non-imaging reflective light concentrator.

Figure 5:
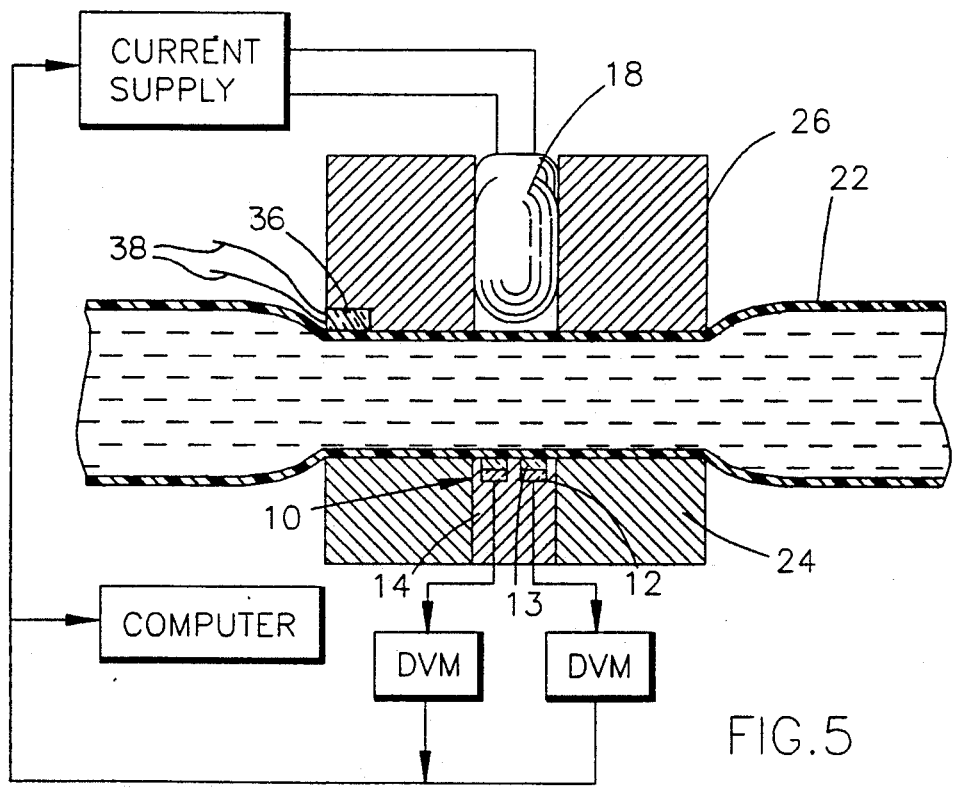
FIG. 5 is a schematic view of the alternating current (AC) electronic detection system currently used with the alcohol sensing device of this invention.

A schematic diagram of the actual measurement system used with the alcohol sensor of this invention is shown in FIG. 5. Specifically, a Hewlett Packard 9816 computer (labeled as Computer) is used as the controller. The Computer is interfaced by an IEEE 488 bus to the instruments used to control the alternating current supplied to the light bulb 18 (labeled "Current Supply") and to measure each thermopile 12a and 12b output voltage (labeled as "DVM"'s). The Current Supply to the light bulb 18 is controlled by the combination of an Electronic Development Corporation Model 3200 Current Calibrator and Model 501J Programmable Voltage Standard. Each of these thermopile detectors is interfaced to a corresponding digital volt meter (DVM). One is a Keithley model 196 system DVM, the other is a Hewlett Packard Model 3478 Multimeter. In operation, the two DVM's could be identical, which would probably be preferred so as to eliminate any discrepancies between the two DVM systems.

In the preferred mode of operation, the Computer (1) sets the light bulb 18 current to a value of 0.8 Amps, waits 200 milliseconds, (2) asks one DVM to measure the voltage from its corresponding thermopile 12a, (3) asks the other DVM to measure the voltage from the other thermopile 12b, (4) then sets the bulb 18 current to 1.2 Amps, waits another 200 milliseconds, (5) again asks the first DVM to measure the voltage from its corresponding thermopile 12a, (6) then the second DVM to measure the voltage from the other thermopile 12b, and (7) begins the cycle again. Concurrently, the temperature of the fuel mixture is being measured using conventional means. Because the light source 18 is emitting light continuously through the fuel mixture within the fuel line 22 and the measurements are occurring almost continuously by the DVM's, the time difference between the measurements by the two DVMs is inconsequential to the resulting ratio of absorbances. Once these signals for the two different wavelengths at both power settings are obtained, the ratio of the amounts of absorption by the alcohol/gasoline fuel mixture at both wavelengths for each power setting is computed. The concentration of alcohol in the fuel is then determined from standard absorption data at a particular fuel temperature. By modulating the light source 18 with an alternating current signal between a high and low power, the ratios are less subject to environmentally-generated noise.

Alternatively, it may be preferred that the measurements be made using a stand alone microprocessor, which may actually be simpler than the current control system. This would be accomplished by switching a single analog-to-digital converter between the two thermopile detectors 12a and 12b, rather than using two separate digital volt meters for measuring the two thermopile 12a and 12b signals. The analog-to-digital converter would require about ten bits of resolution in the 0-20 mV range for successful operation.

During continuous operation, broad band background noise and signal drift were observed from each thermopile detector 12a and 12b, which accordingly limits the accuracy of the resulting measurements. Experiments showed that some of the signal drift was associated with changes in light output from the light bulb 18. This drift was essentially eliminated by taking the ratio of the signals from the two detectors. Also, since each thermopile 12a and 12b essentially measures a temperature difference between itself and the ambient conditions, a constant drift in ambient temperature produces a constant drift in the output voltage, even in the absence of incident infrared radiation to the thermopiles 12a and 12b. Therefore, in order to obtain an accurate electrical signal in the presence of these ambient temperature drifts, some modulation of the signal control must be used. In particular, the drift was diminished by using the Computer, as shown in the preferred control system of FIG. 5, to provide an alternating current signal so as to periodically switch the bulb current between 0.8 and 1.2 Amps while the dc voltage from each of the two thermopiles was recorded with a Digital Volt Meter (DVM). With this approach, the signal drifts were limited to only about 0.1% of the measured ratio of intensities at the two wavelengths of interest, over a time scale of hours. Alternatively, if the light source 18 were operated using a direct current, the noise level could become extremely high over time. In this specific example, the dc output voltage from each thermopile 12a and 12b was about 20 mV for an operating current of about 1.2 Amps through the light bulb 18.

It is also to be noted that a change in filament temperature within the light bulb 18 will in principle lead to a change in the measured ratio of intensities for a fixed alcohol content. Such a change, if it were to occur, say as the bulb 18 ages, would be a source of long term drift because of a change in its "color temperature", which refers to how the relative emission at different wavelengths changes as the temperature of the light source 18 changes. For example, at 2000 K, the filament emits light with nearly equal intensity at the first wavelength centered about 1.3 micrometers and at the second wavelength centered about 1.5 micrometers, while at 2500 K the intensity is around 13% greater at 1.3 micrometers than at 1.5 micrometers. Thus, a large temperature change within the light source 18 could lead to intolerable errors in the ratios of the signals at the two wavelengths. Experimentally, we have determined that changes in the lamp intensity of about 15% at a wavelength of about 1.5 micrometers result in changes in the ratio of detected intensities of around one percent. Therefore, bulb intensity must be kept constant to within about 10%. The simplest approach for accomplishing this was to keep the various currents running through the light bulb 18 constant. This maintains the color temperature of the light bulb 18 as constant so long as the filament within the light bulb 18 is not damaged. Alternative means for accomplishing this would include using a silicon detector in a feed back circuit to maintain constant bulb brightness, or by using a reference filter that passes light in two bands, one greater than 1.5 micrometers, the other less than 1.5 micrometers, so that the resulting color temperature matches the 1.5 micrometer optical filter.

In addition, the alcohol sensor of this invention is equally suitable for use with an alcohol/gasoline fuel mixture which contains either ethanol or methanol. The ratios of the absorption coefficients for ethanol and methanol, are dependent upon the presence of the same O—H bonds within the molecules. These ratios are linearly related to the concentration of either alcohol within the fuel mixture. Therefore, the alcohol sensor of this invention is capable of widespread use with various fuel mixtures.

Therefore, the alcohol sensor of this invention measures the alcohol concentration within a fuel mixture by determining the relative infrared absorbances at two particular wavelengths by the fuel mixture. The sensor includes two thermopile detectors which are disposed so as to receive the emitted light beam at each wavelength after it has been transmitted through the alcohol/gasoline fuel mixture. The first thermopile determines the amount of light absorbance by the fuel mixture at a first wavelength, and similarly, the second thermopile determines the amount of light absorbance by the fuel mixture at the second wavelength. Accordingly each thermopile generates a temperature rise due to the amount of incident light received. Once signals at the two wavelengths are obtained, the ratio between the amounts of absorption by the alcohol/gasoline fuel mixture at both wavelengths is computed and the concentration of alcohol in the fuel is determined.

This alcohol sensor provides several particularly advantageous features. Firstly, this sensor utilizes a single optical path for the absorption measurements at both wavelengths. Therefore, if any component of the sensor degrades, the degradation will equally affect both measurements and since a ratio between the two measurements is the ultimate parameter being measured, the degradation effects will essentially cancel. Further, temperature effects are practically inconsequential since the temperature effects are essentially identical for both of the thermopile detectors, which are extremely small and mounted on a much larger chip which serves as a heat sink, and again any detrimental effects of temperature will accordingly cancel since it is the ratio between the two measurements which is critical. Also, since a light bulb is utilized as the light source, the spectral output of the light bulb is independent of local temperature. Lastly, the number of components and therefore the complexity of the sensor is minimal which thereby lends itself for widespread use including automotive applications.

In addition, there are several potential applications envisioned for this type of infrared sensing device. For example, many properties of normal gasoline fuel, such as the temperature by which half of the gasoline has boiled, aromatic content or octane number, are correlated to the infrared spectra of the fuel and could therefore be determined. In some instances, measurements at more than just two wavelengths may be required. Also, this infrared sensing device could be used to determine the composition of any absorbing medium within the automotive environment. Infrared detection with this sensor could also be used to detect water on the windshield of the automobile so as to instruct the windshield wipers to swipe across the windshield.

Therefore, while our invention has been described in terms of a preferred embodiment, it is apparent that other forms could be readily adopted by one skilled in the art, such as those variations described above or such as the incorporation of fiber optics within the sensor.

Accordingly, the scope of the invention is to be limited only by the following claims.

The embodiments of the invention in which an exclusive property or privilege is claimed are defined as follows:

1. A sensing device for determining the alcohol content of an alcohol/gasoline mixture comprising:

a light source emitting a light beam containing at least a first and a second wavelengths within the near-infrared spectrum, said light beam being transmitted through the alcohol/gasoline fuel mixture;

means for switching the current through said light source between at least two fixed values, so as to correspondingly switch the light intensity at said first and second wavelengths which is emitted by said light source;

first and second detectors which are disposed so as to receive said emitted light beam after its transmission through the alcohol/gasoline fuel mixture, said first detector determines a first amount of absorption by the alcohol/gasoline fuel mixture at said first wavelength for each of said fixed values of current, and said second detector determines a second amount of absorption by the alcohol/gasoline fuel mixture at said second wavelength for each of said fixed values of current;

means for separately measuring the output voltage from said first and second detectors for each of said power settings; and computational means for determining, from said output voltages, the ratio of said first and second absorbances by the alcohol/gasoline fuel mixture at said first and said second wavelengths for each of said fixed values of current such that said ratio of absorbances provide an output indicative of the alcohol content within the alcohol/gasoline mixture.

2. A sensing device for determining the alcohol content of an alcohol/gasoline mixture as recited in claim 1, wherein said first and second detectors are thermopile-type detectors and each of said thermopile-type detectors generates a predetermined voltage corresponding to an increase in their temperature, said increase in temperature caused by incidence of the emitted light at the first and second wavelengths on the surface of each of said corresponding first and second detectors.

3. A sensing device for determining the alcohol content of an alcohol/gasoline mixture as recited in claim 1 wherein said first wavelength is approximately 1.3 micrometers and said second wavelength is approximately 1.5 micrometers.

4. A sensing device for determining the alcohol content of an alcohol/gasoline mixture which is provided via a fuel carrying line to an internal combustion engine for operation of that engine, comprising:

means for measuring the temperature of the alcohol/gasoline mixture..

a current-controlled light source emitting a light beam containing at least a first and a second wavelengths within the near-infrared spectrum, said light beam being transmitted through the alcohol/gasoline mixture within the fuel carrying line;

means for switching the current through said light source between two fixed values, so as to correspondingly switch the light intensity at said first and second wavelengths which is emitted by said light source;

first and second thermopile-type detectors disposed so as to receive said emitted light beam after its transmission through the alcohol/gasoline mixture within the fuel carrying line, said first detector being optically filtered to receive a band of wavelengths centered about said first wavelength so as to determine a first amount of absorbance by the alcohol/gasoline mixture at said first wavelength for each of said fixed current values, and said second detector being optically filtered to receive a band of wavelengths centered about said second wavelength which does not overlap said band centered about said first wavelength so as to determine a second amount of absorbance by the alcohol/gasoline mixture at said second wavelength for each of said fixed current values;

means for separately measuring the output voltage from each of said first and second thermopile-type detectors for each of said fixed current values; and computational means for determining, from said output voltages, the ratio of said first and second absorbances by the alcohol/gasoline fuel mixture at said first and said second wavelengths for each of said fixed current values, wherein said ratio (R) is equal to $(V_{1A}-V_{1B})/(V_{2A}-V_{2B})$, with $V_{1A}$ and $V_{1B}$ being said voltage outputs by said first detector sensing at said first wavelength corresponding to each of said fixed current values respectively, and $V_{2A}$ and $V_{2B}$ being said voltage outputs by said second detector sensing at said second wavelength corresponding to each of said fixed current values respectively;

such that said ratio of absorbances when considered with said temperature of the mixture is indicative of said alcohol content within the alcohol/gasoline mixture.

5. A sensing device for determining the alcohol content of an alcohol/gasoline mixture as recited in claim 4 wherein said first wavelength, the alcohol is significantly more absorbing than the gasoline component of the mixture and at said second wavelength, the alcohol and gasoline components are both essentially non-absorbing.

6. A sensing device for determining the alcohol content of an alcohol/gasoline mixture as recited in claim 5 wherein said first wavelength is approximately 1.3 micrometers and said second wavelength is approximately 1.5 micrometers.

7. A sensing device for determining the alcohol content of an alcohol/gasoline mixture as recited in claim 6 wherein said spectral bands are about 0.2 micrometers wide centered about said first and second wavelengths.

8. A sensing device for determining the alcohol content of an alcohol/gasoline mixture as recited in claim 4 wherein said current through said light source is switched between a value of about 0.8 and about 1.2 Amperes.

9. A sensing device for determining the alcohol content of an alcohol/gasoline mixture containing up to about 85% by volume of alcohol, which is provided via a fuel carrying line to an internal combustion engine for operation of that engine, comprising:

means for measuring the temperature of the alcohol/gasoline mixture;

a current-controlled light source emitting a light beam containing at least a first and a second wavelengths within the near-infrared spectrum, wherein at said first wavelength, the alcohol is significantly more absorbing than the gasoline component of the mixture and at said second wavelength, the alcohol and gasoline components are both essentially non-absorbing, said light beam being transmitted through the alcohol/gasoline mixture over a single optical path of predetermined length through the fuel carrying line;

means for switching the current through said light source between two fixed values, so as to correspondingly switch the light intensity at said first and said second wavelengths which is emitted by said light source;

first and second thermopile-type detectors disposed so as to receive said emitted light beam after its transmission through the alcohol/gasoline mixture within the fuel carrying line, said first detector being optically filtered to receive a spectral band of wavelengths centered about said first wavelength so as to determine a first amount of absorbance by the alcohol/gasoline mixture at said first wavelength for each of said fixed current values, and said second detector being optically filtered to receive a spectral band of wavelengths centered about said second wavelength which does not overlap said band centered around said first wavelength so as to determine a second amount of absorbance by the alcohol/gasoline mixture at said second wavelength for each of said fixed current values;

means for separately measuring the output voltage from each of said first and second thermopile-type detectors for each of said fixed current values; and computational means for determining, from said output voltages, the ratio of said first and second absorbances by the alcohol/gasoline fuel mixture at said first and said second wavelengths for each of said fixed current values, wherein said ratio (R) is equal to $(V_{1A}-V_{1B})/(V_{2A}-V_{2B})$, with $V_{1A}$ and $V_{1B}$ being said voltage outputs by said first detector sensing at said first wavelength corresponding to each of said fixed current values respectively, and $V_{2A}$ and $V_{2B}$ being said voltage outputs by said second detector sensing at said second wavelength corresponding to each of said fixed current values respectively;

such that said ratio of absorbances when considered with said temperature of the mixture is indicative of said alcohol content within the alcohol/gasoline mixture.

10. A sensing device for determining the alcohol content of an alcohol/gasoline mixture as recited in claim 9 wherein said first wavelength is approximately 1.3 micrometers and said second wavelength is approximately 1.5 micrometers.

11. A sensing device for determining the alcohol content of an alcohol/gasoline mixture as recited in claim 10 wherein said spectral bands are about 0.2 micrometers wide centered about said first and second wavelengths.

12. A sensing device for determining the alcohol content of an alcohol/gasoline mixture as recited in claim 9 wherein said predetermined optical path length ranges between one to three millimeters.

13. A sensing device for determining the alcohol content of an alcohol/gasoline mixture as recited in claim 9 wherein said current through said light source is switched between a value of about 0.8 and about 1.2 Amperes.

14. A method for determining the alcohol content of an alcohol/gasoline mixture containing up to about 85% by volume of alcohol, which is provided via a fuel carrying line to an internal combustion engine for operation of that engine, comprising the following steps:

measuring the temperature of the alcohol/gasoline mixture;

emitting a light beam from a current-controlled light source, said light beam containing at least a first and a second wavelengths within the near-infrared spectrum, wherein at said first wavelength, the alcohol is significantly more absorbing than the gasoline component of the mixture and at said second wavelength, the alcohol and gasoline components are both essentially non-absorbing, said light beam being transmitted through the alcohol/gasoline mixture over a single optical path of predetermined length through the fuel carrying line;

switching the current through said light source between two fixed values, so as to correspondingly switch the light intensity at said first and said second wavelengths which is emitted by said light source;

detecting at a first and second detector said emitted light beam after transmission through the alcohol/gasoline mixture within the fuel carrying line, said first detector being optically filtered to receive a spectral band of wavelengths centered about said first wavelength so as to determine a first amount of absorbance by the alcohol/gasoline mixture at said first wavelength for each of said fixed current values, and said second detector being optically filtered to receive a spectral band of wavelengths centered about said second wavelength which does not overlap said band centered around said first wavelength so as to determine a second amount of absorbance by the alcohol/gasoline mixture at said second wavelength for each of said fixed current values, said first and second detectors each generating an output voltage proportional to the incident light it receives at each of said wavelengths for each of said fixed current values;

separately measuring the output voltage from each of said first and second detectors for each of said fixed current values; and computing from said output voltages, the ratio of said first and second absorbances by the alcohol/gasoline fuel mixture at said first and said second wavelengths for each of said fixed current values, wherein said ratio (R) is equal to $(V_{1A}-V_{1B})/(V_{2A}-V_{2B})$, with $V_{1A}$ and $V_{1B}$ being said voltage outputs by said first detector sensing at said first wavelength corresponding to each of said fixed current values respectively, and $V_{2A}$ and $V_{2B}$ being said voltage outputs by said second detector sensing at said second wavelength corresponding to each of said fixed current values respectively;

such that said ratio of absorbances when considered with said temperature of the mixture is indicative of said alcohol content within the alcohol/gasoline mixture.

15. A method for determining alcohol content of an alcohol/gasoline mixture as recited in claim 14 wherein said first wavelength is approximately 1.3 micrometers and said second wavelength is approximately 1.5 micrometers.

16. A method for determining the alcohol content of an alcohol/gasoline mixture as recited in claim 15 wherein said spectral bands are about 0.2 micrometers wide centered about said first and second wavelengths.

17. A method for determining the alcohol content of an alcohol/gasoline mixture as recited in claim 14 wherein said predetermined optical path length ranges between one to three millimeters.

18. A method for determining the alcohol content of an alcohol/gasoline mixture as recited in claim 14 wherein said current through said light source is switched between a value of about 0.8 and about 1.2 Amperes.

* * * * *